US010653611B2

(12) United States Patent
Alves et al.

(10) Patent No.: US 10,653,611 B2
(45) Date of Patent: May 19, 2020

(54) HAIR CARE COMPOSITION COMPRISING AMINO SILICONE, FATTY ALCOHOL AND PARAFFIN OIL

(71) Applicant: L'OREAL, Paris (FR)

(72) Inventors: Diego Alves, Rio de Janeiro (BR); Alice Matos Xavier, Rio de Janeiro (BR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/915,707

(22) PCT Filed: Sep. 2, 2013

(86) PCT No.: PCT/BR2013/000342
§ 371 (c)(1),
(2) Date: Mar. 1, 2016

(87) PCT Pub. No.: WO2015/027302
PCT Pub. Date: Mar. 5, 2015

(65) Prior Publication Data
US 2016/0206547 A1 Jul. 21, 2016

(51) Int. Cl.
A61K 8/898 (2006.01)
A61Q 5/12 (2006.01)
A61K 8/41 (2006.01)
A61K 8/34 (2006.01)
A61K 8/31 (2006.01)
A61Q 5/00 (2006.01)

(52) U.S. Cl.
CPC ............... *A61K 8/898* (2013.01); *A61K 8/31* (2013.01); *A61K 8/342* (2013.01); *A61K 8/416* (2013.01); *A61Q 5/12* (2013.01); *A61K 2800/592* (2013.01); *A61Q 5/002* (2013.01)

(58) Field of Classification Search
CPC ........ A61K 8/416; A61K 8/898; A61Q 5/002; A61Q 5/12
See application file for complete search history.

(56) References Cited

U.S. PATENT DOCUMENTS 5,580,494 A * 12/1996 Sandhu ................ A61K 8/31
510/125
2009/0074699 A1* 3/2009 Biganska ............ A61K 8/8152
424/70.16
2011/0182839 A1* 7/2011 Numata ................ A61K 8/416
424/62

FOREIGN PATENT DOCUMENTS

DE 295 309 A5 10/1991
DE 10 2006 039 801 A1 2/2008
DE 102006039801 * 2/2008 ............... A61K 8/37
WO 2012/024364 A2 2/2012

OTHER PUBLICATIONS

"Hair Pack", GNPD, Total 2 Pages, (Aug. 2011), XP002723774.
"Cys-Treatment Straightening Hair Treatment", GNPD, Total 2 Pages, (Jun. 2011), XP002723775.
"SILSOFT* AX conditioning agent", Marketing Bulletin, Momentive, pp. 1-12, (Mar. 2012), XP002723776.
International Search Report and Written Opinion dated Jun. 23, 2014 in PCT/BR13/000342 Filed Sep. 2, 2013.

* cited by examiner

*Primary Examiner* — Anna R Falkowitz
(74) *Attorney, Agent, or Firm* — Oblon, McClelland, Maier & Neustadt, L.L.P.

(57) ABSTRACT

The present invention relates to a cosmetic composition, especially a haircare composition for conditioning the hair, which comprises an amino silicone, a cationic surfactant, a fatty alcohol comprising 8 to 30 carbon atoms, and a hydrocarbon-based oil. The invention also relates to a treatment process for keratin substances, in particular for conditioning hair, implementing said cosmetic composition.

6 Claims, No Drawings

HAIR CARE COMPOSITION COMPRISING AMINO SILICONE, FATTY ALCOHOL AND PARAFFIN OIL

The present invention relates to a cosmetic composition, in particular a hair composition, comprising amino silicones, cationic surfactants and fatty substances, and also to a cosmetic treatment process implementing it, in particular for conditioning the hair.

Hair that has been sensitized, embrittled or damaged by the action of atmospheric agents or by mechanical or chemical treatments, such as dyeing, bleaching and/or permanent waving, is often difficult to disentangle and to style and generally lacks softness. One solution for overcoming these problems is to use conditioners, in particular cationic surfactants, cationic polymers, fatty substances or silicones, to make hair easier to disentangle and to make it soft and supple. These conditioners improve the disentangling and softness of wet and dried hair, but may, however, have a tendency to make the hair lank and dull.

Haircare compositions such as rinse-off hair conditioners, and leave-on masks, creams and milks, are generally emulsions with varying degrees of thickness. They afford the hair good cosmetic properties; however, users sometimes feel that their hair is lank and that it becomes greasy easily, especially if they have fine hair. It may also prove to be difficult to distribute the composition evenly when it is applied to the hair.

Oily sera and hair oils for improving the sleekness of the hair from a visual point of view, especially by reducing the frizziness, while at the same time imparting manageability and a certain level of control of the volume of the head of hair, have also been proposed. However, the performance of these products is still not optimal, especially from the point of view of the efficacy in reducing the frizziness, the ease of application of the composition, the ability to convey other active materials and the final cosmeticity of the treated hair.

Consumers are therefore still in search of optimized compositions, for obtaining adequate visual sleekness of the hair; good feel of the hair, and in particular of wet hair; control, or even elimination, of frizziness, and also control or reduction of the volume and of the apparent mass of the head of hair, the said compositions thus being most particularly suitable for curly and/or voluminous hair.

The object of the present invention is to propose a cosmetic composition that has improved working properties, which applies easily to the hair, and also affords good conditioning properties to the head of hair, especially in terms of a soft feel, suppleness, sleekness and disentangling.

A subject of the present invention is thus a cosmetic composition comprising:
one or more amino silicones,
one or more cationic surfactants,
at least 3% by weight of one or more fatty alcohols comprising 8 to 30 carbon atoms, and
one or more hydrocarbon-based oils.

It was observed that the composition has a creamy texture that feels pleasant and is easy to apply to the hair; this composition spreads well on the hair and also rinses out easily and quickly.

It gives the head of hair softness, sleekness and suppleness; it in particular affords a natural, healthy feel to sensitized or embrittled hair, both to wet hair and dry hair, giving it a very satisfactory final cosmetic state.

It is particularly suitable for use on curly hair and enables shiny and supple curls to be obtained.

It most particularly affords sleekness to the head hair, which is reflected by a disappearance of frizziness, and control of the volume of the head of hair, or even reduction of its apparent volume, allowing better control of the head of hair.

In the present description, the term "at least one" is equivalent to the term "one or more" and may be replaced therewith; the term "comprised between" is equivalent to the term "ranging from" and may be replaced therewith, which implies that the limits are included.

Amino Silicones

The cosmetic composition according to the invention comprises one or more amino silicones. The term "amino silicone" is intended to mean any silicone comprising at least one primary, secondary or tertiary amine or a quaternary ammonium group.

The weight-average molecular weights of these amino silicones can be measured by gel permeation chromatography (GPC) at room temperature (25° C.), as polystyrene equivalents. The columns used are µ styragel columns. The eluent is THF and the flow rate is 1 ml/minute. 200 µl of a solution containing 0.5% by weight of silicone in THF are injected. Detection is performed by refractometry and UV-metry.

As amino silicone that may be used in the scope of the invention, the following can be cited:
a) polysiloxanes corresponding to formula (A):

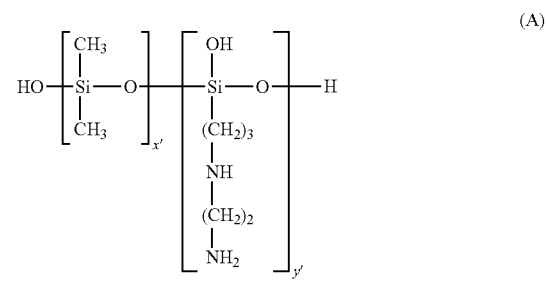

in which x' and y' are integers such that the weight-average molecular weight (Mw) is comprised between about 5000 and 500 000;

b) amino silicones corresponding to formula (B):

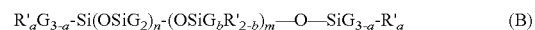

in which:
G, which may be identical or different, designate a hydrogen atom, or a phenyl, OH or $C_1$-$C_8$ alkyl group, for example methyl, or $C_1$-$C_8$ alkoxy, for example methoxy,
a, which may be identical or different, denote the number 0 or an integer from 1 to 3, in particular 0;
b denotes 0 or 1, and in particular 1;
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
R', which may be identical or different, denote a monovalent radical having formula —$C_qH_{2q}$L in which q is a number ranging from 2 to 8 and L is an optionally quaternized amino group chosen from the following groups:

—NR"—Q—N(R")$_2$
—N(R")$_2$
—N$^+$(R")$_3$A—
—N$^+$H(R")$_2$A—
—N$^+$H$_2$(R") A—
—N(R")—Q—N$^+$R"H$_2$A—
—NR"—Q—N$^+$(R")$_2$H A—
—NR"—Q—N$^+$(R")$_3$A—, in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A– represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

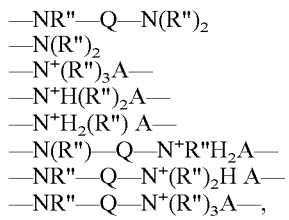

in which n and m have the meanings given above, in formula B.

Another group of amino silicones corresponding to this definition is represented by silicones having the following formulae (D) or (E):

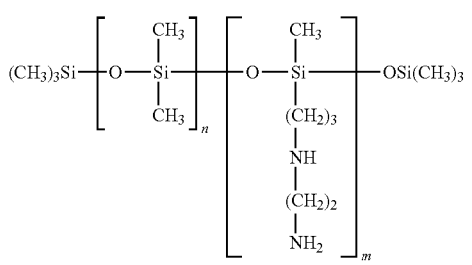

in which:
m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;
R1, R2, R3, which may be identical or different, represent a hydroxy or $C_1$-$C_4$ alkoxy radical, where at least one of the radicals R1 to R3 denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

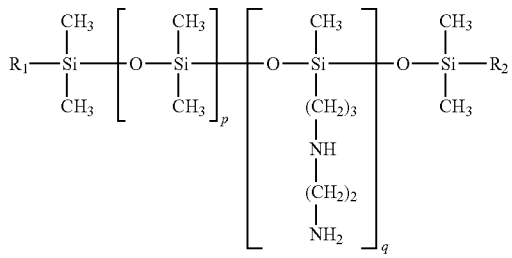

in which:
p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;
R1, R2, which are different, represent a hydroxy or $C_1$-$C_4$ alkoxy radical, where at least one of the radicals R1 or R2 denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

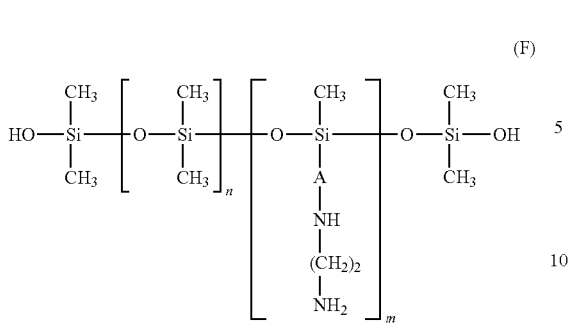

(F)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A silicone having this formula is for example DC2-8299 Cationic Emulsion by Dow Corning.

Another group of amino silicones corresponding to this definition is represented by the following formula (G):

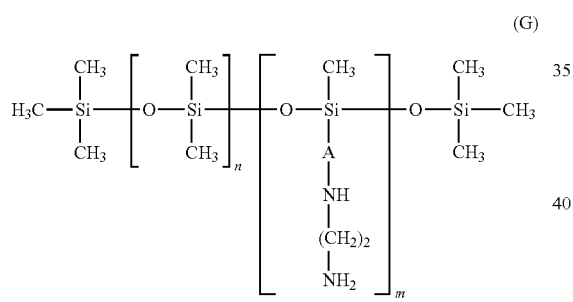

(G)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

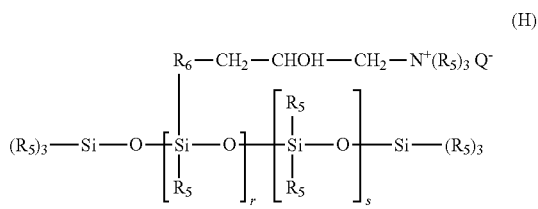

(H)

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q– is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in patent U.S. Pat. No. 4,185,087.

d) quaternary ammonium silicones having formula (I):

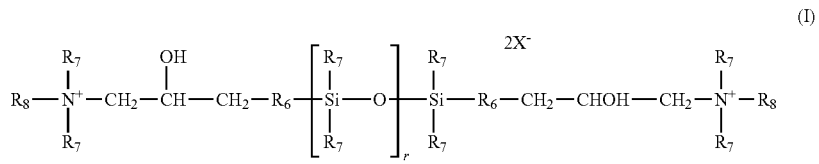

(I)

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

$X^-$ is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

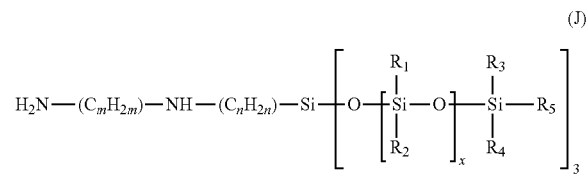

in which:
R$_1$, R$_2$, R$_3$ and R$_4$, which may be identical or different, denote a $C_1$-$C_4$ alkyl radical or a phenyl group;
R$_5$ denotes a $C_1$-$C_4$ alkyl radical or a hydroxyl group;
n is an integer ranging from 1 to 5;
m is an integer ranging from 1 to 5;
and in which x is chosen such that the amine number is between 0.01 and 1 meq/g;

f) multiblock polyoxyalkylenated amino silicones, of type (AB)n, A being a polysiloxane block and B being a polyoxyalkylenated block containing at least one amine group.

Said silicones are preferably constituted of repeating units having the following general formulae:

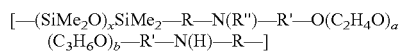

or alternatively

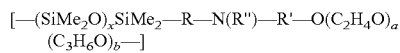

in which:
a is an integer greater than or equal to 1, preferably ranging from 5 to 200, more particularly ranging from 10 to 100;
b is an integer comprised between 0 and 200, preferably ranging from 4 to 100, more particularly between from 5 and 30;
x is an integer ranging from 1 to 10 000, more particularly from 10 to 5000;
R″ is a hydrogen atom or a methyl;
R, which may be identical or different, represent a divalent linear or branched C2-C12 hydrocarbon-based radical, optionally including one or more heteroatoms such as oxygen; preferably, R denotes an ethylene radical, a linear or branched propylene radical, a linear or branched butylene radical, or a —CH2CH2CH2OCH(OH)CH2— radical; preferentially R denotes a —CH2CH2CH2OCH(OH)CH2— radical;
R', which may be identical or different, represent a divalent linear or branched C2-C12 hydrocarbon-based radical, optionally including one or more heteroatoms such as oxygen; preferably, R' denotes an ethylene radical, a linear or branched propylene radical, a linear or branched butylene radical, or a CH2CH2CH2OCH(OH)CH2— radical; preferentially R' denotes —CH(CH3)—CH2—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft A-843 or Silsoft A+ by Momentive.

g) the alkylamino silicones corresponding to formula (K) below:

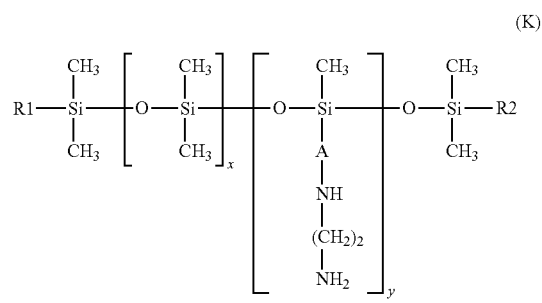

in which:
x and y are numbers ranging from 1 to 5000; preferably, x ranges from 10 to 2000 and especially from 100 to 1000; preferably, y ranges from 1 to 100;
R1 and R2, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
A denotes a linear or branched alkylene radical containing from 2 to 8 carbon atoms,
Preferably, A comprises 3 to 6 carbon atoms, especially 4 carbon atoms; preferably, A is branched. Mention may be made especially of the following divalent radicals: —CH$_2$CH$_2$CH$_2$— and —CH$_2$CH(CH$_3$)CH$_2$—.
Preferably, R1 and R2, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R1 and R2, which may be identical or different, are chosen from hexadecyl (cetyl) and octadecyl (stearyl) radicals.

Preferentially, the silicone is of formula (K) with:
x ranging from 10 to 2000 and especially from 100 to 1000;
y ranging from 1 to 100;
A comprising 3 to 6 carbon atoms and especially 4 carbon atoms; preferably, A is branched; and more particularly A is chosen from the following divalent radicals: —CH$_2$CH$_2$CH$_2$— and —CH$_2$CH(CH$_3$)CH$_2$—; and
R1 and R2, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, R1 and R2, which may be identical or different, being chosen from hexadecyl (cetyl) and octadecyl (stearyl) radicals.

A preferred silicone of formula (K) is bis-cetearyl amodimethicone (INCI name).

Mention may be made especially of the silicone sold under the name Silsoft AX by Momentive.

Preferably, the amino silicones according to the invention are chosen from the amino silicones of formula (K).

The composition according to the invention preferably comprises the amino silicone(s) in an amount ranging from 0.05% to 10% by weight, preferably from 0.1% to 5% by weight and preferentially from 0.5% to 3% by weight, relative to the total weight of the composition.

Cationic Surfactants

The cosmetic composition according to the invention also comprises one or more cationic surfactants. They are advantageously chosen from optionally polyoxyalkylenated primary, secondary or tertiary fatty amine salts, quaternary ammonium salts, and mixtures thereof.

As quaternary ammonium salts, mention may be made in particular of:

quaternary ammonium salts having formula (Ia):

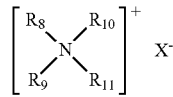

(Ia)

in which:

the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ containing from 8 to 30 carbon atoms and preferably from 12 to 24 carbon atoms; it being possible for the aliphatic groups to comprise heteroatoms such as, in particular, oxygen, nitrogen, sulfur or halogens;

The aliphatic groups are chosen, for example, from $C_1$-$C_{30}$ alkyl, $C_1$-$C_{30}$ alkoxy, ($C_2$-$C_6$)polyoxyalkylene, $C_1$-$C_{30}$ alkylamide, ($C_{12}$-$C_{22}$)alkyl($C_2$$C_6$)alkylamido, ($C_{12}$-$C_{22}$)alkyl acetate and $C_1$-$C_{30}$ hydroxyalkyl groups.

$X^-$ is an anion chosen from the group consisting of halides, phosphates, acetates, lactates, ($C_1$-$C_4$)alkyl sulfates, ($C_1$-$C_4$)alkylsulfonates and ($C_1$-$C_4$)alkylarylsulfonates.

Among the quaternary ammonium salts having formula (Ia), preference is firstly given to tetraalkylammonium chlorides such as, for example, dialkyldimethylammonium or alkyltrimethylammonium chlorides in which the alkyl group comprises approximately from 12 to 22 carbon atoms, particularly behenyltrimethylammonium, distearyldimethylammonium, cetyltrimethylammonium, and benzyldimethylstearylammonium chlorides, or secondly, to palmitylamidopropyltrimethylammonium chloride or stearamidopropyldimethyl(myristyl acetate)-ammonium chloride, which is sold under the name Ceraphyl® 70 by the company Van Dyk.

imidazoline quaternary ammonium salts having formula (Ib):

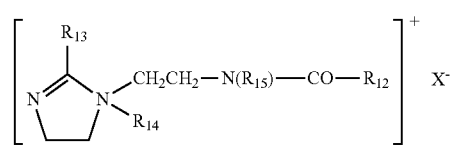

in which $R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ is an anion chosen from the group consisting of halides, phosphates, acetates, lactates, ($C_1$-$C_4$)alkyl sulfates, ($C_1$-$C_4$)alkylsulfonates and ($C_1$-$C_4$)alkylarylsulfonates;

$R_{12}$ and $R_{13}$ preferably denote a mixture of alkenyl or alkyl groups containing from 12 to 21 carbon atoms, for example fatty acid derivatives of tallow, $R_{14}$ denotes a methyl group, and $R_{15}$ denotes a hydrogen atom. A product of this kind is sold for example under the name Rewoquat® W 75 by the company Rewo.

quaternary di- or triammonium salts having formula (IIIb):

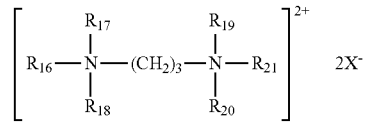

in which $R_{16}$ denotes an alkyl group containing approximately from 16 to 30 carbon atoms, which is optionally hydroxylated and/or interrupted with one or more oxygen atoms, $R_{17}$ is chosen from hydrogen or an alkyl group containing from 1 to 4 carbon atoms or a group $—(CH_2)_3—N^+(R_{16a})(R_{17a})$ $(R_{18a})$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$ is an anion chosen from the group consisting of halides, acetates, phosphates, nitrates, ($C_1$-$C_4$)alkyl sulfates, ($C_1$-$C_4$)alkylsulfonates and ($C_1$-$C_4$)alkylarylsulfonates, in particular methyl sulfate and ethyl sulfate. Such compounds are, for example, Finquat CT-P, sold by the company Finetex (Quaternium 89), and Finquat CT, sold by the company Finetex (Quaternium 75), quaternary ammonium salts containing one or more ester functions having the following formula (IVb):

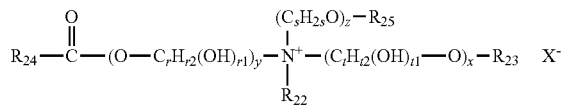

in which:

$R_{22}$ is chosen from $C_1$-$C_6$ alkyl groups and $C_1$-$C_6$ hydroxyalkyl or $C_1$-$C_6$ dihydroxyalkyl groups;

$R_{23}$ is chosen from the group $R_{26}$—C(═O)—; hydrocarbon-based linear or branched, saturated or unsaturated $C_1$-$C_{22}$ groups $R_{27}$; and a hydrogen atom;

$R_{25}$ is chosen from the group $R_{28}$—C(═O)—; hydrocarbon-based linear or branched, saturated or unsaturated $C_1$-$C_6$ groups $R_{29}$; and a hydrogen atom;

$R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

r1 and t1, which may be identical or different, are equal to 0 or 1;

r2+r1=2 r and t1+t2=2 t;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear. Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is an $R_{27}$ hydrocarbon group, it may be long and may have from 12 to 22 carbon atoms, or may be short and may have from 1 to 3 carbon atoms.

When $R_{25}$ is an $R_{29}$ hydrocarbon group, it preferably has 1 to 3 carbon atoms.

Advantageously, $R_{24}$, $R_{26}$ and $R_{28}$, which are identical or different, are chosen from linear or branched, saturated or unsaturated $C_{11}$-$C_{21}$ hydrocarbon groups, and more particularly from linear or branched, saturated or unsaturated $C_{11}$-$C_{21}$ alkyl and alkenyl groups.

Preferably, x and z, which may be identical or different, are equal to 0 or 1. Advantageously, y is equal to 1. Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate, ($C_1$-$C_4$)alkyl sulfonate or ($C_1$-$C_4$)alkylaryl sulfonate.

However, it is possible to use methanesulfonate, phosphate, nitrate, tosylate, an anion derived from an organic acid, such as acetate or lactate, or any other anion that is compatible with the ammonium comprising an ester function.

The anion $X^-$ is more particularly still chloride, methyl sulfate or ethyl sulfate.

Use is made more particularly, in the composition according to the invention, of the ammonium salts having formula (IVb) in which:

$R_{22}$ denotes a methyl or ethyl group, x and y are equal to 1, z is equal to 0 or 1, r, s and t are equal to 2, $R_{23}$ is chosen from the group $R_{26}$—C(═O)—; methyl groups, ethyl groups or hydrocarbon-based $C_{14}$-$C_{22}$ groups; and a hydrogen atom, $R_{25}$ is chosen from the group $R_{28}$—C(═O)—; and a hydrogen atom, $R_{24}$, $R_{26}$ and $R_{28}$, which may be identical or different, are chosen from linear or branched, saturated or unsaturated $C_{13}$-$C_{17}$ hydrocarbon groups, and preferably from linear or branched, saturated or unsaturated $C_{13}$-$C_{17}$ alkyl and alkenyl groups.

The hydrocarbon-based groups are advantageously linear.

Among the compounds of formula (IVb), examples that may be mentioned include salts, in particular the chloride or methyl sulfate of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent, such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts. Use may also be made of the ammonium salts containing at least one ester function that are described in patents U.S. Pat. Nos. 4,874,554 and 4,137,180. Use may also be made of behenoylhydroxypropyltrimethylammonium chloride, for example, sold by the company Kao under the name Quartamin BTC 131.

Preferably, the ammonium salts containing at least one ester function contain two ester functions.

Preferably, the cationic surfactants are chosen from cetyltrimethylammonium, behenyltrimethylammonium, and dipalmitoylethylhydroxyethylmethylammonium salts, and mixtures thereof, and more particularly from behenyltrimethylammonium chloride or methosulfate, cetyltrimethylammonium chloride or methosulfate, and dipalmitoylethylhydroxyethylammonium chloride or methosulfate, and mixtures thereof. Even more preferentially, the cationic surfactant is a behenyltrimethylammonium salt.

The composition according to the invention preferably comprises the cationic surfactant(s) in an amount ranging from 0.1% to 10% by weight, preferably from 0.5% to 8% by weight and preferentially from 1% to 5% by weight, relative to the total weight of the composition.

Fatty Alcohol

The cosmetic composition according to the invention also comprises one or more fatty alcohols comprising 8 to 30 carbon atoms, which may be liquid at 25° C. and at 1 atmosphere, or alternatively may be solid.

They are advantageously non-glycerolated and non-oxyalkylenated, and may be saturated or unsaturated.

They preferably correspond to the formula R—OH in which R is a saturated or unsaturated, linear or branched hydrocarbon-based radical, comprising 8 to 30 carbon atoms, optionally comprising one or more OH groups.

Preferably, R comprises from 10 to 22 carbon atoms, or even from 12 to 20 carbon atoms.

Preferably, R is a saturated, linear or branched radical.

The saturated liquid fatty alcohols are preferably branched. They can optionally comprise, in their structure, at least one aromatic or non-aromatic ring. They are preferably acyclic. Among liquid saturated fatty alcohols, octyldodecanol, isostearyl alcohol and 2-hexyldecanol can be cited.

The unsaturated liquid fatty alcohols exhibit, in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They are preferably acyclic. Among the liquid unsaturated fatty alcohols, oleyl alcohol, linoleyl alcohol, linolenyl alcohol and undecylenyl alcohol may be mentioned.

The solid fatty alcohols that may be used are preferably chosen from linear, saturated alcohols containing from 8 to 30 carbon atoms. Mention may be made of myristyl alcohol, cetyl alcohol, stearyl alcohol and their mixture, cetylstearyl alcohol.

Preferably, the composition comprises one or more solid, saturated linear fatty alcohols, comprising 8 to 30 carbon atoms, chosen especially from myristyl alcohol, cetyl alcohol, stearyl alcohol and cetylstearyl alcohol.

The composition according to the invention comprises the fatty alcohol(s) in an amount of greater than or equal to 3% by weight, relative to the total weight of the composition.

Preferably, it comprises the fatty alcohol(s) in an amount ranging from 3% to 10% by weight, preferably from 3.5% to 8% by weight, preferentially from 3.8% to 7% by weight and better still from 4% to 6% by weight, relative to the total weight of the composition.

Hydrocarbon-Based Oil

The cosmetic composition according to the invention also comprises one or more hydrocarbon-based oils that are advantageously liquid at 25° C. and 1 atmosphere.

The term "hydrocarbon-based oil" means an oil whose structure comprises only carbon and hydrogen atoms. These oils are thus saturated or unsaturated, linear, branched or cyclic hydrocarbons, and may be of mineral, plant, animal or synthetic origin.

The following may especially be mentioned:
  linear or branched C6-C32 and especially C8-C24 alkanes, and especially C6-C32 and especially C8-C24 isoparaffins; mention may thus be made of hexane, undecane, dodecane, tridecane, isohexadecane, isodecane, isodecane, paraffin oil (liquid paraffin), petroleum jelly, petroleum jelly oil (liquid petroleum jelly) and squalane;
  saturated or unsaturated, linear or branched hydrocarbons comprising at least 16 carbon atoms, such as polydecenes and hydrogenated polyisobutene, especially the product sold under the brand name Parleam® by the company NOF Corporation.

Preferably, the composition comprises one or more hydrocarbon-based oils chosen from linear or branched C6-C32 and especially C8-C24 alkanes.

The composition according to the invention preferably comprises the hydrocarbon-based oil(s) in an amount ranging from 0.1% to 20% by weight, preferably from 0.5% to 15% by weight, better still from 1% to 10% by weight, even better still from 1.5% to 8% by weight and preferentially from 2% to 5% by weight, relative to the total weight of the composition.

In a particularly preferred embodiment of the invention, the composition according to the invention comprises the fatty alcohol(s) and the hydrocarbon-based oil(s) in a total amount of at least 4.5% by weight relative to the total weight of the composition, especially in an amount ranging from 4.5% to 20% by weight, or even from 5% to 15% by weight and most particularly from 5% to 10% by weight.

This means that the sum of the total amount of fatty alcohols and of the total amount of hydrocarbon-based oils preferably represents at least 4.5% by weight relative to the total weight of the cosmetic composition according to the invention.

Additional Non-Silicone Fatty Substance

The composition according to the invention may advantageously comprise one or more additional non-silicone fatty substances, other than the above fatty alcohols and hydrocarbon-based oils.

The term "fatty substance" means an organic compound that is insoluble in water at room temperature (25° C.) and at atmospheric pressure (1 atm), i.e. solubility of less than 5% by weight, preferably less than 1% by weight.

They are generally soluble in organic solvents under the same temperature and pressure conditions, for instance chloroform, ethanol, benzene, liquid petroleum jelly or decamethylcyclopentasiloxane.

The term "non-silicone fatty substance" means a fatty substance whose structure does not comprise any silicon atoms. The non-silicone fatty substances generally have in their structure a hydrocarbon-based chain comprising at least 6 carbon atoms and not comprising any siloxane groups.

The non-silicone fatty substances may be liquid or solid at room temperature and atmospheric pressure (25° C., 1 atm).

Preferably, the composition may advantageously comprise one or more non-silicone fatty substances chosen from fatty acid and/or fatty alcohol esters, fatty ethers, non-silicone waxes other than fatty alcohols, and mixtures thereof.

The liquid fatty esters are preferably esters derived from a $C_6$-$C_{32}$ fatty acid and/or a $C_6$-$C_{32}$ fatty alcohol, and are liquid at 25° C., 1 atm. Preferably, these are liquid esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbon atoms in the esters being greater than or equal to 10. Preferably, for the esters of monoalcohols, at least one of the alcohol or the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate and diethylene glycol diisononanoate.

Mention may also be made of sugar esters and diesters of $C_6$-$C_{30}$ and preferably $C_{12}$-$C_{22}$ fatty acids. It is recalled that the term "sugar" means oxygenated hydrocarbon-based compounds containing several alcohol functions, with or without aldehyde or ketone functions, and which comprise at least 4 carbon atoms. These sugars can be monosaccharides, oligosaccharides or polysaccharides. Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose. The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds. The esters according to this variant may also be chosen from mono-, di-, tri- and tetraesters, and polyesters, and mixtures thereof. These esters may be, for example, oleates, laurates, palmitates, myristates, behenates, cocoates, stearates, linoleates, linolenates, caprates and arachidonates, and mixtures thereof, such as, in particular, oleopalmitate, oleostearate or palmitostearate mixed esters. More particularly, use is made of monoesters and diesters and in particular of sucrose, glucose or methylglucose mono- or dioleates, stearates, behenates, oleopalmitates, linoleates, linolenates or oleostearates. An example that may be mentioned is the product sold under the name Glucate® DO by the company Amerchol, which is a methylglucose dioleate.

Finally, use may also be made of natural or synthetic glycerol esters of mono-, di- or triacids. Among these, mention may be made of plant oils. As oils of plant origin or synthetic triglycerides that may be used in the composition of the invention as liquid fatty esters, the following can be cited, for example: triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, safflower oil, candlenut oil, camellina oil, tamanu oil, babassu oil and pracaxi oil, caprylic/capric acid triglycerides, for instance those sold by the company Stéarineries Dubois or those sold under the names Miglyol® 810, 812 and 818 by the company Dynamit Nobel, jojoba oil and shea butter oil.

As solid fatty acid esters and/or fatty alcohol esters mention may be made of solid esters obtained from $C_9$-$C_{26}$ fatty acids and from $C_9$-$C_{26}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate and stearyl myristate, and hexyl stearate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used. Mention may be made in particular of diethyl sebacate, diisopropyl sebacate, diisopropyl adipate, di-n-propyl adipate, dioctyl adipate and dioctyl maleate.

The liquid fatty ethers may be chosen from liquid dialkyl ethers such as dicaprylyl ether. The non-liquid fatty ethers are preferably chosen from dialkyl ethers and in particular dicetyl ether and distearyl ether, alone or as a mixture.

The non-silicone waxes are chosen in particular from carnauba wax, candelilla wax, esparto wax, paraffin wax, ozokerite, plant waxes such as olive tree wax, rice wax, hydrogenated jojoba wax or absolute flower waxes, such as the blackcurrant blossom essential wax sold by Bertin (France), or animal waxes such as beeswaxes or modified beeswaxes (cerabellina), and ceramides.

Ceramides or ceramide analogues such as glycoceramides, which can be used in the compositions according to the invention, are known per se and are natural or synthetic molecules which may conform to the general formula below:

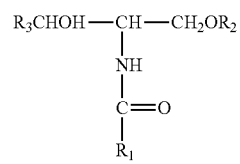

in which:
R$_1$ denotes a linear or branched, saturated or unsaturated alkyl group which derives from $C_{14}$-$C_{30}$ fatty acids, it being possible for this group to be substituted in alpha position by a hydroxyl group, or in omega position by a hydroxyl group which is esterified with a saturated or unsaturated $C_{16}$-$C_{30}$ fatty acid;
R$_2$ denotes a hydrogen atom or a (glycosyl)n, (galactosyl)m or sulfogalactosyl group, in which n is an integer from 1 to 4 and m is an integer from 1 to 8;
R$_3$ denotes a $C_{15}$-$C_{26}$ hydrocarbon group which is saturated or unsaturated in alpha position, it being possible for this group to be substituted by one or more $C_1$-$C_{14}$ alkyl groups;
with the proviso that, in the case of natural ceramides or glycoceramides, R$_3$ may also denote a $C_{15}$-$C_{26}$ α-hydroxyalkyl group, the hydroxyl group being optionally esterified with a $C_{16}$-$C_{30}$ α-hydroxy acid.

The ceramide or ceramides that are more particularly preferred according to the invention are the compounds for which R$_1$ denotes a saturated or unsaturated alkyl derived from $C_{16}$-$C_{22}$ fatty acids; R$_2$ denotes a hydrogen atom; and R$_3$ denotes a saturated linear $C_{15}$ group. Such compounds are, for example, N-linoleyldihydrosphingosine, N-oleyldihydrosphingosine, N-palmityldihydrosphingosine, N-stearyldihydrosphingosine or N-behenyldihydrosphingosine, or mixtures of these compounds.

Preferably, ceramides are used for which R$_1$ denotes a saturated or unsaturated alkyl group derived from $C_{14}$-$C_{30}$ fatty acids; R$_2$ denotes a galactosyl or sulfogalactosyl group; and R$_3$ denotes a —CH=CH—(CH$_2$)$_{12}$—CH$_3$ group.

Preferably, the composition may comprise one or more non-silicone fatty substances chosen from fatty esters, in particular $C_8$-$C_{30}$ fatty esters, in particular liquid fatty esters; plant oils and in particular triglyceride oils of plant origin; and ceramides.

The composition may comprise the additional non-silicone fatty substance(s) in an amount preferably between 0.01% and 15% by weight, especially from 0.1% to 10% by weight and better still between 0.5% and 5% by weight, relative to the total weight of the composition.

The composition according to the invention may be provided in any galenical form conventionally used and in particular in the form of an aqueous, alcoholic or aqueous-alcoholic solution or suspension or oily solution or suspension; of a dispersion of the lotion or serum type; of an emulsion, in particular having a liquid or semi-liquid consistency, of the O/W, W/O or multiple type; of an aqueous or anhydrous gel, or of any other cosmetic form. Preferably, the composition according to the invention is a cream.

Preferably, the composition according to the invention has a viscosity at 25° C. and at a shear rate of 1 s$^{-1}$ preferably ranging from 400 cps to 10 000 cps (centipoises). This viscosity may be measured using a viscometer with cone-plate geometry. Preferentially, the composition according to the invention has such a viscosity and is a cream.

The composition according to the invention is preferably aqueous and then comprises water at a concentration preferably ranging from 25% to 99% by weight, especially from 40% to 98% by weight and better still from 60% to 97% by weight, relative to the total weight of the composition.

The pH of the composition may range from 2.5 to 8, preferentially between 7 and 3, or even between 3 and 5.

The composition according to the invention may optionally comprise one or more organic solvents that are liquid at 25° C. and 1 atmosphere, and preferably hydrophilic (soluble or miscible in water), which may be chosen from $C_1$-$C_6$ aliphatic or aromatic monoalcohols, $C_2$-$C_8$ polyols, and $C_3$-$C_7$ polyol ethers. Advantageously, the organic solvent is chosen from C2-C4 mono-, di- or tri-diols. It can advantageously be chosen from among ethanol, isopropanol, benzyl alcohol, glycerol, propane-1,2-diol (propylene glycol) and mixtures thereof.

The composition according to the invention may also comprise at least one or more common cosmetic ingredients chosen especially from surfactants, especially anionic and nonionic surfactants; thickeners, gelling agents; polymers, especially cationic polymers; sunscreens; moisturizers; anti-dandruff agents; antioxidants; chelating agents; reducing agents; oxidation bases, couplers, oxidizing agents, direct dyes; relaxants; nacreous agents and opacifiers; micas, nacres, glitter flakes; plasticizers or coalescers; hydroxy acids; pigments; fillers; fragrances; basifying or acidifying agents; silanes. A person skilled in the art will take care to choose the ingredients included in the composition and the amounts thereof so that they do not harm the properties of the compositions of the present invention.

The cosmetic composition according to the invention in particular finds a particularly advantageous application in the hair sector, especially for caring for and/or conditioning the hair. The haircare compositions are preferably conditioners, styling or treatment gels, treatment or conditioning lotions or creams, masks. Advantageously, the composition according to the invention is in the form of a conditioning product that can be rinsed off or left on.

The cosmetic composition may or may not be rinsed out after having been applied to the keratin materials, in particular the hair. It is thus optionally possible to perform rinsing, for example with water, after an optional leave-in time. Preferably, it is rinsed out, after an optional leave-in time.

A subject of the invention is also a cosmetic treatment process, especially for caring for and/or conditioning keratin substances, especially the hair, comprising the application to the said keratin substances of a cosmetic composition according to the invention, optionally followed by rinsing, after an optional leave-in time.

Preferably, this is a hair treatment process, particularly for caring for and/or conditioning hair, especially curly hair, or even sensitized, embrittled and/or damaged hair.

The present invention is illustrated in greater detail in the examples that follow (% AM=percentage of active material in the composition).

EXAMPLE 1

A hair composition for conditioning the hair is prepared, comprising (% by weight):

|  | % by weight |
|---|---|
| Bis-cetearyl amodimethicone | 1.8% |
| Behenyltrimethylammonium chloride (Genamin KDMP) | 2% AM |
| Cetylstearyl alcohol (30/70) | 4% |
| Hydrocarbon-based oil (liquid paraffin) | 2% |
| Preserving agents, fragrance | qs |
| Water | qs 100% |

A thick, stable haircare cream that is particularly suitable for sensitized or damaged hair is obtained.

It is easy to apply and spreads well and evenly over the hair; the hair has a more pleasant feel, whether during application to wet hair, or after drying, when the hair is dry.

A reduction in the apparent volume of the head of hair and a reduction of frizziness are also observed.

The invention claimed is:

1. A cosmetic composition comprising:
   bis-cetearyl amodimethicone present in an amount of from 0.5% to 3% by weight, relative to a total weight of the composition;
   1% to 5% by weight, relative to a total weight of the composition of a cationic surfactant selected from the group consisting of a cetyltrimethylammonium salt, a behenyltrimethylammonium salt, and a dipalmitoylethylhydroxyethylammonium salt;
   4% to 6% by weight, relative to a total weight of the composition of one or more fatty alcohols selected from the group consisting of stearyl alcohol, cetyl alcohol, cetylstearyl alcohol, and a combination thereof; and
   1 to 10% by weight, relative to a total weight of the composition of a hydrocarbon-based oil selected from the group consisting of a linear or branched C6-C32 alkane; and a saturated or unsaturated, linear or branched hydrocarbon comprising at least 16 carbon atoms; wherein
   a pH of the composition is from 2.5 to 5.0,
   the composition does not comprise any of an oxidation base, a coupler, an oxidizing agent and a direct dye, and
   the composition does not comprise a cationic polymer which is not an amino silicone.

2. The composition of claim 1, farther comprising a linear or branched C6-C32 alkane.

3. The composition of claim 1, comprising water at a concentration ranging from 25% to 99% by weight, relative to a total weight of the composition.

4. The composition of claim 1, having a viscosity at 25° C. and at a shear rate of 1 s$^{-1}$ ranging from 400 cps to 10 000 cps.

5. A process for caring for and/or conditioning a keratin substance, comprising applying the composition of claim 1 to the keratin substance.

6. The process of claim 5, wherein the keratin substance is hair.

\* \* \* \* \*

UNITED STATES PATENT AND TRADEMARK OFFICE
CERTIFICATE OF CORRECTION

PATENT NO. : 10,653,611 B2
APPLICATION NO. : 14/915707
DATED : May 19, 2020
INVENTOR(S) : Diego Alves et al.

Page 1 of 1

It is certified that error appears in the above-identified patent and that said Letters Patent is hereby corrected as shown below:

In the Claims

In Column 18, Line 60, Claim 2, delete "farther" and insert -- further --, therefor.

Signed and Sealed this
First Day of September, 2020

Andrei Iancu
*Director of the United States Patent and Trademark Office*